(12) United States Patent
Ohashi et al.

(10) Patent No.: US 10,147,511 B2
(45) Date of Patent: Dec. 4, 2018

(54) RADIOLUCENT WINDOW, RADIATION DETECTOR AND RADIATION DETECTION APPARATUS

(71) Applicant: HORIBA, Ltd., Kyoto-shi, Kyoto (JP)

(72) Inventors: Satoshi Ohashi, Kyoto (JP); Yoshiaki Nakata, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/494,058

(22) Filed: Apr. 21, 2017

(65) Prior Publication Data

US 2017/0229206 A1 Aug. 10, 2017

Related U.S. Application Data

(63) Continuation of application No. 14/621,056, filed on Feb. 12, 2015, now Pat. No. 9,666,323.

(30) Foreign Application Priority Data

Feb. 18, 2014 (JP) .................................. 2014-028671

(51) Int. Cl.
*H01J 5/18* (2006.01)
*G21K 1/10* (2006.01)
(Continued)

(52) U.S. Cl.
CPC ............. *G21K 1/10* (2013.01); *G01N 23/223* (2013.01); *G01N 23/2252* (2013.01); *H01J 37/244* (2013.01); *H01J 2237/24415* (2013.01)

(58) Field of Classification Search
CPC .... G01N 23/223; G01N 23/2252; G21K 1/10; H01J 35/18; H01J 37/244; H01J 5/18; H01J 2237/24415
(Continued)

(56) References Cited

U.S. PATENT DOCUMENTS 5,509,046 A * 4/1996 Logan .................... F27D 21/02
                                                                250/505.1
7,737,424 B2 * 6/2010 Xu ........................... H01J 5/18
                                                                250/374
(Continued)

FOREIGN PATENT DOCUMENTS

JP    H03-135787 A    6/1991
JP    07-333399 A    12/1995
(Continued)

OTHER PUBLICATIONS

Office Action dated Sep. 19, 2017 from the corresponding Japanese Application No. JP 2014-028671.

*Primary Examiner* — Courtney Thomas
(74) *Attorney, Agent, or Firm* — Lucas & Mercanti, LLP (57) ABSTRACT

Linear ribs are formed radially with a center at a through-hole on one face of an X-ray transmissive film (radiolucent film) in an X-ray transmissive window (radiolucent window) to be used for an X-ray detector (radiation detector). The X-ray transmissive window faces a sample. A beam for irradiation to the sample passes through the through-hole, and X-rays (radiation) are radially emitted on a line extending through the through-hole and enter the X-ray transmissive window. Since the linear ribs are formed radially with the center at the through-hole, even X-rays entering at shallow angles with respect to the X-ray transmissive window are transmitted through the X-ray transmissive window at a probability equivalent to X-rays entering at deep angles. More X-rays are transmitted through the X-ray transmissive window, and thus the X-ray detector can detect X-rays with high efficiency.

10 Claims, 11 Drawing Sheets

(51) Int. Cl.
  *G01N 23/223* (2006.01)
  *G01N 23/2252* (2018.01)
  *H01J 37/244* (2006.01)

(58) Field of Classification Search
  USPC .......................................................... 378/140
  See application file for complete search history.

(56) References Cited

U.S. PATENT DOCUMENTS

| | | |
|---|---|---|
| 2009/0028297 A1 | 1/2009 | Matoba et al. |
| 2010/0200750 A1 | 8/2010 | Mantz et al. |
| 2012/0213336 A1* | 8/2012 | Liddiard ................. G21K 1/02 |
| | | 378/161 |
| 2013/0000253 A1* | 1/2013 | Berg ....................... H01J 33/04 |
| | | 53/425 |
| 2013/0051535 A1 | 2/2013 | Davis et al. |
| 2013/0279654 A1 | 10/2013 | Kantonen et al. |

FOREIGN PATENT DOCUMENTS

| | | |
|---|---|---|
| JP | 2000-206299 A | 7/2000 |
| JP | 2010-182679 A | 8/2010 |
| JP | 2012-242381 A | 12/2012 |
| JP | 2013-519086 A | 5/2013 |
| JP | 2014-240770 A | 12/2014 |
| JP | 2016-211850 A | 12/2016 |
| WO | 2013/138258 A1 | 9/2013 |

\* cited by examiner

RADIOLUCENT WINDOW, RADIATION DETECTOR AND RADIATION DETECTION APPARATUS

CROSS-REFERENCE TO RELATED APPLICATIONS

This Nonprovisional application is a Continuation of U.S. patent application Ser. No. 14/621,056, filed on Feb. 12, 2015, which claims priority under 35 U.S.C. §119(a) on Patent Application No. 2014-028671 filed in Japan on Feb. 18, 2014, the entire contents of which are hereby incorporated by reference.

BACKGROUND

1. Technical Field

The present invention relates to: a radiolucent window, which transmits radiation entering a radiation detector; a radiation detector; and a radiation detection apparatus.

2. Description of Related Art

Some X-ray detectors use a detection element, such as an SDD (Silicon Drift Detector), which requires cooling. For such an X-ray detector, vacuum sealing or dry gas enclosing is performed in order to prevent dew condensation in the detection element. Therefore, an X-ray detector is provided with an X-ray transmissive window, which transmits X-rays and can withstand a differential pressure between inside of the X-ray detector and the atmosphere. Conventional structures of an X-ray transmissive window are mainly divided into two types. A first type of an X-ray transmissive window is a thin film (having a thickness of several μm to several tens μm) made of a material, which satisfactorily transmits X-rays and has high intensity and high toughness. The material to be used is a metal, such as beryllium, which has a small atomic number. A second type of an X-ray transmissive window is obtained by holding an organic film, which is made of polyimide or the like, or a CVD (Chemical Vapor Deposition) film (having a thickness of several tens μm to several hundreds μm), which is made of diamond or $Si_3N_4$ or the like, with a rib, which is made of silicon or diamond and has a beam structure (having a height of several hundreds μm).

The first type of an X-ray transmissive window has a large thickness and thus hardly transmits X-rays of 1 keV or lower. The second type of an X-ray transmissive window is superior in that a part having no rib can transmit even X-rays of 1 keV or lower. However, in a case where an X-ray enters obliquely with respect to an X-ray transmissive window, the X-ray is blocked by a rib and cannot be transmitted through the X-ray transmissive window. U.S. Pat. No. 7,737,424 discloses an X-ray transmissive window wherein the probability that an X-ray is blocked is lowered by devising the form of a rib so that the aperture ratio with respect to the incident direction of X-rays becomes higher. Regarding a conventional X-ray detection apparatus, an X-ray emission source and an X-ray detector are located sufficiently away from each other and X-rays enter substantially perpendicularly with respect to an X-ray transmissive window, and thus there is only a small influence of a rib on the detection efficiency of X-rays.

SUMMARY OF THE INVENTION

In an X-ray detection apparatus for detecting X-rays generated from a sample irradiated with radiation, e.g., an apparatus for detecting fluorescent X-rays, an X-ray detector is sometimes located close to a sample in order to enhance the detection efficiency of X-rays. In such an X-ray detection apparatus, X-rays enter obliquely with respect to an X-ray transmissive window. As the angle at which an X-ray enters the X-ray transmissive window becomes shallower, the probability that the X-ray is blocked by a rib of the X-ray transmissive window becomes higher, and thus the detection efficiency of the X-ray lowers. In a case where one point on a sample is irradiated with radiation and X-rays are detected, X-rays are generated from the one point on the sample and thus enter at a plurality of angles both in an in-plane rotation angle direction of the X-ray transmissive window and in an elevation angle with respect to the plane. Even in an X-ray transmissive window obtained by devising the form of a rib so that the aperture ratio with respect to a specific incident direction becomes higher, in a case where X-rays enter from a plurality of directions, a rib blocks X-rays entering from directions other than a direction in which the aperture ratio is made higher, and thus the detection efficiency of X-rays lowers.

The present invention has been made in view of such a situation, and the object thereof is to provide: a radiolucent window for effectively detecting radiation generated radially; a radiation detector; and a radiation detection apparatus.

A radiolucent window according to the present invention is characterized by comprising: a film which transmits radiation; and a plurality of ribs formed on one face of the film, wherein the plurality of ribs include a plurality of first ribs formed radially with a center at the predetermined one point.

A radiolucent window according to the present invention is characterized in that the plurality of ribs include at least one second rib, which is formed to intersect the plurality of first ribs and the number of which is smaller than the plurality of first ribs.

A radiolucent window according to the present invention is characterized in that the plurality of ribs include a third rib which is formed to intersect the plurality of first ribs and has a smaller height from the one face than the plurality of first ribs.

A radiolucent window according to the present invention is characterized in that the plurality of ribs include a plurality of fourth ribs formed parallel to any of the plurality of first ribs.

A radiolucent window according to the present invention is characterized in that a larger number of ribs are formed in a region on the one face far from the predetermined one point than in a region close to the predetermined one point.

A radiolucent window according to the present invention is characterized in that the one face includes: a first region in the vicinity of the predetermined one point; and a second region at a greater distance from the predetermined one point than the first region, a mesh rib is formed in the first region, and the plurality of first ribs are formed in the second region.

A radiation detector according to the present invention is characterized by comprising: a radiolucent window according to the present invention; and an element for detecting radiation transmitted through the radiolucent window.

A radiation detection apparatus according to the present invention is characterized by comprising: an irradiation unit for irradiating a sample with a beam; and a radiation detector according to the present invention for detecting radiation generated from a part on the sample irradiated with the beam.

A radiation detection apparatus according to the present invention is characterized in that the radiation detector has a through-hole which allows passage of the beam, and one point at a center of a plurality of first ribs radially formed in a radiolucent window according to the present invention is included in the through-hole.

In the present invention, a radiolucent window to be used for a radiation detector is provided with a plurality of first ribs radially formed on one face of a radiolucent film. The probability that the first ribs block radiation entering radially with respect to the radiolucent window does not change according to the incidence angle of radiation. Therefore, even when radiation enters at a shallow angle, the radiation is transmitted through the radiolucent window with a probability equivalent to radiation entering at a deep angle.

In the present invention, the radiolucent window is provided with at least one second rib intersecting a plurality of radial first ribs, and the number of the second rib(s) is smaller than the first ribs. Although the second rib(s) intersecting the first ribs blocks radiation entering at a shallow angle, the number of the second rib(s) is small, and thus the probability that radiation is blocked is kept low.

In the present invention, the radiolucent window is provided with a third rib intersecting a plurality of radial first ribs, and the third rib has a smaller height than the first ribs. Although the third rib intersecting the first ribs blocks radiation entering at a shallow angle, the third rib has a small height, and thus the probability that radiation is blocked is kept low.

In the present invention, the radiolucent window is provided with a plurality of radial first ribs and fourth ribs parallel to the first ribs. Even when radiation entering radially with respect to the radiolucent window enters at a shallow angle, the probability that the fourth ribs parallel to the first ribs block radiation is sufficiently low. Therefore, even when radiation enters at a shallow angle, the radiation is transmitted through the radiolucent window with a sufficiently high probability.

In the present invention, the radiolucent window has a larger number of ribs in a region far from the center of the radial first ribs than in a region close to the center. Thus, density lowering of ribs in a region far from the center is prevented.

In the present invention, the radiolucent window is provided with; a mesh rib in a first region in the vicinity of the center of the radial first ribs; and a plurality of first ribs formed in a second region farer from the center than the first region. The incidence angle of radiation entering the first region is deep, and the probability that the mesh rib blocks radiation is low. Although the incidence angle of radiation entering the second region is shallow, the probability that the first ribs block radiation is low.

In the present invention, the detection efficiency of radiation is enhanced with a radiation detector and a radiation detection apparatus wherein radiation entering a radiolucent window at a shallow angle is transmitted through the radiolucent window with a high probability and radiation transmitted through the radiolucent window is detected.

In the present invention, a radiation detection apparatus is provided with a through-hole, which is formed at a radiation detector provided with a radiolucent window and allows passage of a beam for radiation to a sample. It becomes possible to locate the radiation detector as close to the sample as possible by locating the radiation detector between a beam source and the sample.

With the present invention, radiation radially generated from a sample is transmitted through a radiolucent window with a high probability and is detected by a radiation detector even when the radiation enters the radiolucent window at a shallow angle. Therefore, the present invention provides an excellent effect that a radiation detection apparatus can detect radiation with high efficiency by locating the radiation detector as close to a sample as possible.

The above and further objects and features of the invention will more fully be apparent from the following detailed description with accompanying drawings.

DETAILED DESCRIPTION

The following description will concretely explain the present invention with reference to the drawings illustrating some embodiments thereof.

Embodiment 1

Figure 1:
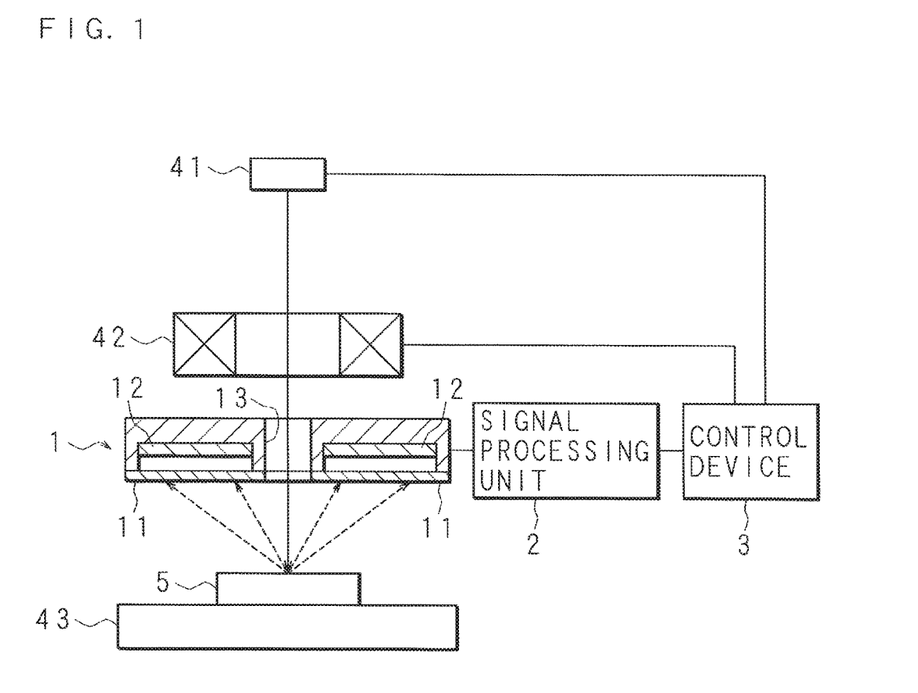
FIG. 1 is a block diagram illustrating the structure of an X-ray spectroscopic analyzer according to Embodiment 1.

FIG. 1 is a block diagram illustrating the structure of an X-ray spectroscopic analyzer (radiation detection apparatus) according to Embodiment 1. The X-ray spectroscopic analyzer is provided with an electron gun 41 for irradiating a sample 5 with an electron ray (beam), an electron lens system 42, and a sample stage 43 on which the sample 5 is to be mounted. The electron lens system 42 includes a scanning coil which changes the direction of an electron ray. The electron gun (irradiation unit) 41 and the electron lens system 42 are connected with a control device 3 for controlling the entire X-ray spectroscopic analyzer.

An X-ray detector (radiation detector) 1 is located between the electron lens system 42 and the sample stage 43. The X-ray detector 1 is formed to have a through-hole 13 which allows passage of an electron ray. FIG. 1 illustrates a section of the X-ray detector 1. Moreover, the X-ray detector 1 includes a plurality of X-ray detection elements 12, such as SDDs. The X-ray detector 1 has a structure wherein the plurality of X-ray detection elements 12 are arranged to surround the through-hole 13. Moreover, the X-ray detector 1 is provided with an X-ray transmissive window (radiolucent window) 11, and the X-ray transmissive window 11 is located at a position to cover the front of the X-ray detection elements 12. Moreover, the X-ray detector 1 is provided with an unillustrated cooling mechanism, such as a Peltier device. The X-ray detector 1 is sealed with the X-ray transmissive window 11. Inside the X-ray detector 1, the pressure is reduced or a predetermined gas is enclosed. The X-ray detector 1 is located at a position where an electron ray passes through the through-hole 13 and is located so that the X-ray transmissive window 11 intersects the axis of the electron ray and the X-ray transmissive window 11 faces the sample stage 43. In a state where a sample 5 is mounted on the sample stage 43, the X-ray detector 1 is located in front of a face of the sample 5 to be irradiated with an electron ray, and the X-ray transmissive window 11 faces the sample 5 and is located between the sample 5 and the X-ray detection elements 12.

In response to a control signal from the control device 3, the electron gun 41 emits an electron ray and the electron lens system 42 sets the direction of the electron ray, so that the electron ray passes through the through-hole 13 of the X-ray detector 1 and the sample 5 on the sample stage 43 is irradiated with the electron ray. Characteristic X-rays are generated at a part on the sample 5 irradiated with the electron ray. The characteristic X-rays are transmitted through the X-ray transmissive window 11, enter the X-ray detector 1, and are detected by the X-ray detection elements 12. An electron ray is indicated by a solid arrow, and characteristic X-rays are indicated by dashed arrows in FIG. 1. The X-ray detector 1 outputs signals proportional to the energy of characteristic X-rays detected by the X-ray detection elements 12. At least the electron gun 41, the electron lens system 42, the X-ray detector 1 and the sample stage 43 in the structure of the X-ray spectroscopic analyzer are accommodated in an unillustrated vacuum chamber. The vacuum chamber is made of material for shielding from electron rays and X-rays, and inside of the vacuum chamber is kept in vacuum during operation of the X-ray spectroscopic analyzer.

The X-ray detector 1 is connected with a signal processing unit 2 for processing an outputted signal. The signal processing unit 2 accepts signals outputted from the X-ray detector 1, counts signals for each value, and performs processing to generate a spectrum of characteristic X-rays which correlates the energy of characteristic X-rays indicated by the value of a signal and a count number with each other. The signal processing unit 2 is connected with the control device 3. The electron lens system 42 sequentially changes the direction of an electron ray, so that the electron ray scans the sample 5. As the electron ray scans the sample 5, characteristic X-rays generated from a part on the sample 5 irradiated with the electron ray are sequentially detected by the X-ray detector 1. By sequentially performing signal processing, the signal processing unit 2 sequentially generates a spectrum of characteristic X-rays generated at a plurality of parts on the sample 5 irradiated with an electron ray, and sequentially outputs data of the generated spectrum of characteristic X-rays to the control device 3. The control device 3 is constituted of a computer, such as a personal computer. The control device 3 accepts the data of a spectrum of characteristic X-rays, and generates distribution of a spectrum of characteristic X-rays generated on the sample 5. The control device 3 can accept an operation by the user and output a detection result of characteristic X-rays. It is to be noted that the control device 3 may perform processing to specify the type and the amount of elements included in the sample 5 from the spectrum of characteristic X-rays and generate element distribution on the sample 5.

Figure 2:
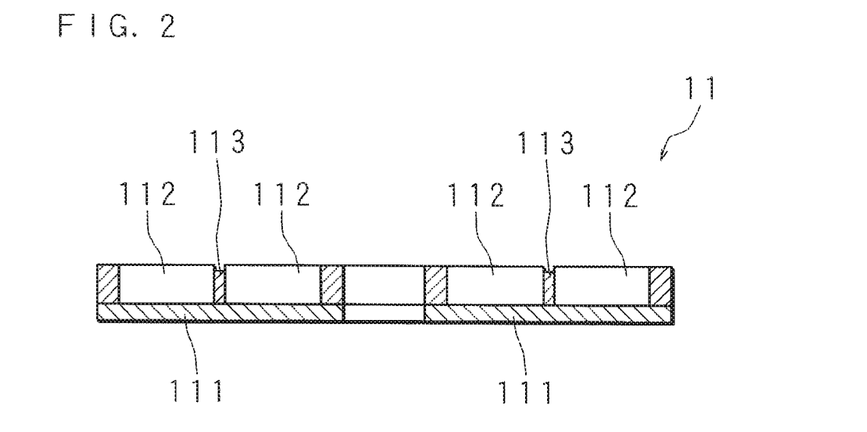
FIG. 2 is a schematic sectional view of an X-ray transmissive window.
Figure 3:
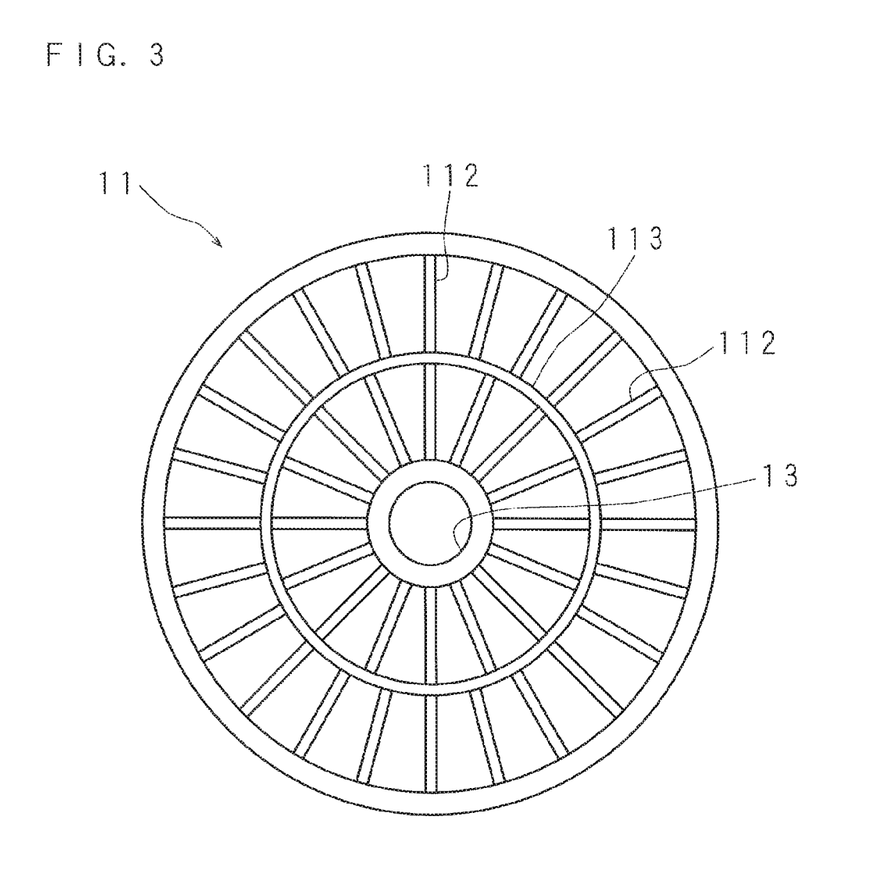
FIG. 3 is a schematic plan view of an X-ray transmissive window according to Embodiment 1.

FIG. 2 is a schematic sectional view of the X-ray transmissive window 11, and FIG. 3 is a schematic plan view of the X-ray transmissive window 11 according to Embodiment 1. The X-ray transmissive window 11 includes an X-ray transmissive film 111, and a plurality of ribs formed on one face of the X-ray transmissive film 111. Moreover, the through-hole 13 is formed also at the X-ray transmissive window 11. The X-ray transmissive film 111 is constituted of an organic film or a CVD film, and has a thickness of several tens μm. The plurality of ribs are formed in contact with one face of the X-ray transmissive film 111, supports the X-ray transmissive film 111, and maintains the structure of the X-ray transmissive film 111. The ribs are made of silicon or diamond, and have a height from the surface of the X-ray transmissive film 111 of several tens μm to several hundreds μm. As illustrated in FIG. 3, the plurality of ribs include a plurality of linear ribs (first ribs) 112, which are formed radially with the center at the through-hole 13, and an annular rib 113, which is formed to surround the through-hole 13. The center point of the radial linear ribs 112 is included in the through-hole 13. The center point of the radial linear ribs 112 is preferably at the center of the through-hole 13 or on the central axis of the electron ray. The plurality of linear ribs 112 are arranged at intervals in the circumferential direction without a rib of another type sandwiched therebetween. The X-ray transmissive film 111 exists at parts between the plurality of linear ribs 112 illustrated in FIG. 3. The annular rib 113 is located so that the through-hole 13 is placed at the center thereof, and intersects the plurality of linear ribs 112. Ribs intersecting the plurality of linear ribs 112 are formed also around the through-hole 13 and at a peripheral part of the X-ray transmissive film 111. The number of the annular rib 113 is smaller than the number of the linear ribs 112. Moreover, the X-ray transmissive film 111 includes a region closer to the through-hole 13 than the annular rib 113, and a region farer from the through-hole 13 than the annular rib 113. A larger number of linear ribs 112 are formed in the region farer from the through-hole 13 than the annular rib 113, than in the region closer to the through-hole 13 than the annular rib 113. By forming a larger number of linear ribs 112 in the region farer from the through-hole 13 than the annular rib 113, it becomes possible to prevent density lowering of the linear ribs 112 and pressure resistance degradation of the X-ray transmissive film 111. Moreover, as illustrated in FIG. 2, the annular rib 113 has a smaller height from the surface of the X-ray transmissive film 111 than the linear ribs 112. The X-ray transmissive window 11 is located so that X-rays enter one of both faces of the X-ray transmissive film 111 where ribs are not formed. It is to be noted that the X-ray transmissive window 11 may be located so that X-rays enter a face of the X-ray transmissive film 111 where ribs are formed. The annular rib 113 corresponds to the second rib and the third rib in the present invention.

Figure 4A:
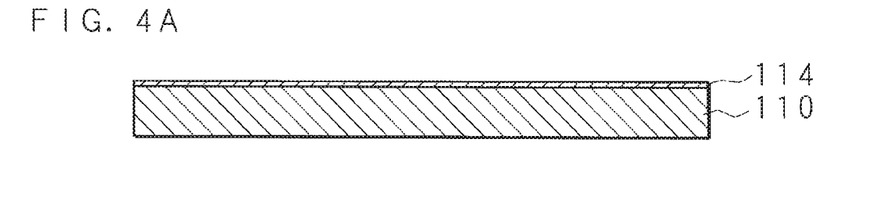
FIG. 4A is a schematic view illustrating a manufacturing method of an X-ray transmissive window.
Figure 4B:
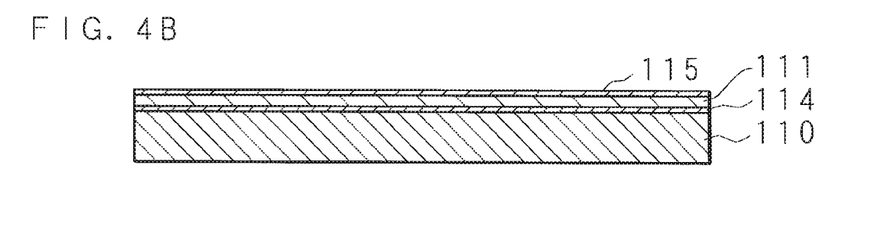
FIG. 4B is a schematic view illustrating a manufacturing method of an X-ray transmissive window.
Figure 4C:
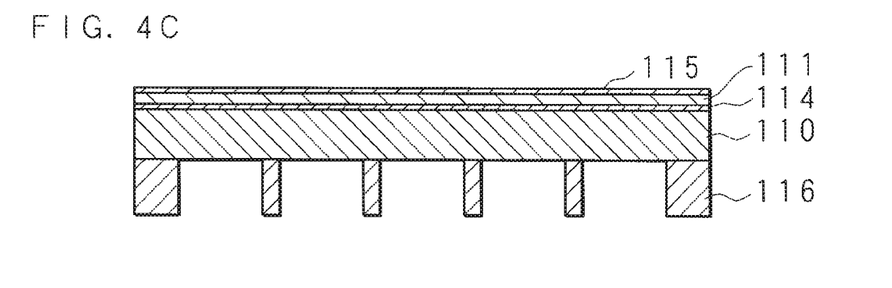
FIG. 4C is a schematic view illustrating a manufacturing method of an X-ray transmissive window.
Figure 4D:
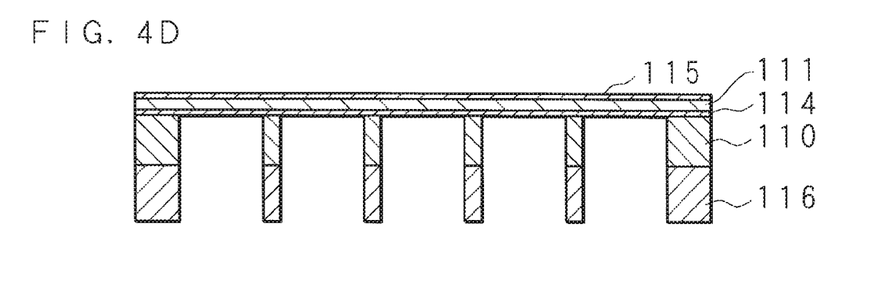
FIG. 4D is a schematic view illustrating a manufacturing method of an X-ray transmissive window.
Figure 4E:
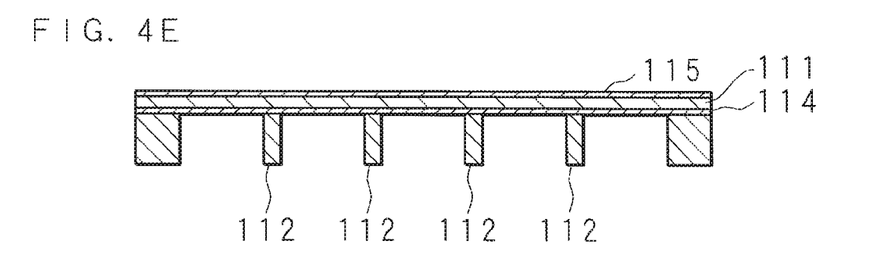
FIG. 4E is a schematic view illustrating a manufacturing method of an X-ray transmissive window.

FIG. 4A, FIG. 4B, FIG. 4C, FIG. 4D and FIG. 4E are schematic views illustrating an example of a manufacturing method of the X-ray transmissive window 11. As illustrated in FIG. 4A, an etching stop layer 114 is generated from $Si_3N_4$ or the like on the surface of a silicon substrate 110. Next, as illustrated in FIG. 4B, the X-ray transmissive film 111 is generated on the etching stop layer 114, and a top coat 115 is generated from aluminum or the like on the X-ray transmissive film 111. Next, as illustrated in FIG. 4C, a pattern of the linear ribs 112 and the annular rib 113 is generated with a resist 116 on the reverse face of the silicon substrate 110. Next, as illustrated in FIG. 4D, the silicon substrate 110 is etched. Next, as illustrated in FIG. 4E, the resist 116 is removed. Parts of the silicon substrate 110 which remain unetched form the linear ribs 112 and the annular rib 113.

Characteristic X-rays generated at the sample 5 are emitted from one point irradiated with an electron ray toward all directions. As seen from the X-ray detector 1, the characteristic X-rays are emitted radially with a center at a line extending through the through-hole 13 from one point on the line, pass through the X-ray transmissive window 11, and enter the X-ray detector 1. As illustrated in FIG. 1, the characteristic X-rays enter at deeper angles with respect to the X-ray transmissive window 11 as the distance from a position where the characteristic X-rays enter the X-ray transmissive widow 11 to the through-hole 13 becomes shorter, and the characteristic X-rays enter at shallower angles with respect to the X-ray transmissive window 11 as the distance from a position where the characteristic X-rays enter the X-ray transmissive window 11 to the through-hole 13 becomes longer. Since the linear ribs 112 are formed radially with the center at the through-hole 13, the probability that the linear ribs 112 block characteristic X-rays entering radially with a center at a line extending through the through-hole 13 does not change according to the incidence angles of the characteristic X-rays. That is, even characteristic X-rays entering at shallow angles with respect to the X-ray transmissive window 11 are also transmitted through the X-ray transmissive window 11 with a probability equivalent to characteristic X-rays entering perpendicularly with respect to the X-ray transmissive window 11. Accordingly, more characteristic X-rays are transmitted through the X-ray transmissive window 11 and detected by the X-ray detection elements 12 than in a case where a conventional X-ray transmissive window is used, and thus the detection efficiency of characteristic X-rays is enhanced.

The annular rib 113 blocks characteristic X-rays entering at shallow angles with respect to the X-ray transmissive window 11. However, since the number of the annular rib 113 is small, the number of ribs to block characteristic X-rays entering at shallow angles is smaller in the X-ray transmissive window 11 than in a conventional X-ray transmissive window. Moreover, since the annular rib 113 has a smaller height from the surface of the X-ray transmissive film 111 than the linear ribs 112, the probability that characteristic X-rays entering at shallow angles are blocked is low. Accordingly, the probability that characteristic X-rays entering at shallow angles with respect to the X-ray transmissive window 11 are blocked is sufficiently lower than a conventional X-ray transmissive window, and thus the detection efficiency of characteristic X-rays is enhanced.

In the X-ray spectroscopic analyzer, although the intensity of characteristic X-rays to be detected becomes higher as the position of the X-ray detector 1 becomes closer to the sample 5, more characteristic X-rays enter at shallow angles with respect to the X-ray transmissive window 11. The detection rate of characteristic X-rays entering at shallow angles with respect to the X-ray transmissive window 11 is higher in the X-ray detector 1 than in a case where a conventional X-ray transmissive window is used, and thus a demerit to be caused by locating the X-ray detector 1 closer to the sample 5 is small. Consequently, the X-ray spectroscopic analyzer enables to locate the X-ray detector 1 as close to the sample 5 as possible, and thus the detection efficiency of characteristic X-rays is enhanced. Accordingly, the X-ray spectroscopic analyzer in this embodiment can detect characteristic X-rays generated from the sample 5 with high efficiency.

It is to be noted that the X-ray transmissive window 11 may be provided with a plurality of annular ribs 113 having different diameters, and the X-ray transmissive film 111 may include three or more regions located at different distances from the through-hole 13. Moreover, the signal processing unit 2 may be designed to execute part of processing of the control device 3, or the control device 3 may be designed to execute part of processing of the signal processing unit 2. Moreover, the X-ray spectroscopic analyzer may have a form wherein the signal processing unit 2 and the control device 3 are integrated. Moreover, the X-ray spectroscopic analyzer may be incorporated in an SEM (Scanning Electron Microscope) or a TEM (Transmission Electron Microscope). Such an X-ray spectroscopic analyzer is provided with a detector for detecting electrons, such as reflected electrons, secondary electrons or transmitted electrons, and with a signal processing unit for processing signals from the detector for the SEM or the TEM.

Embodiment 2

Figure 5:
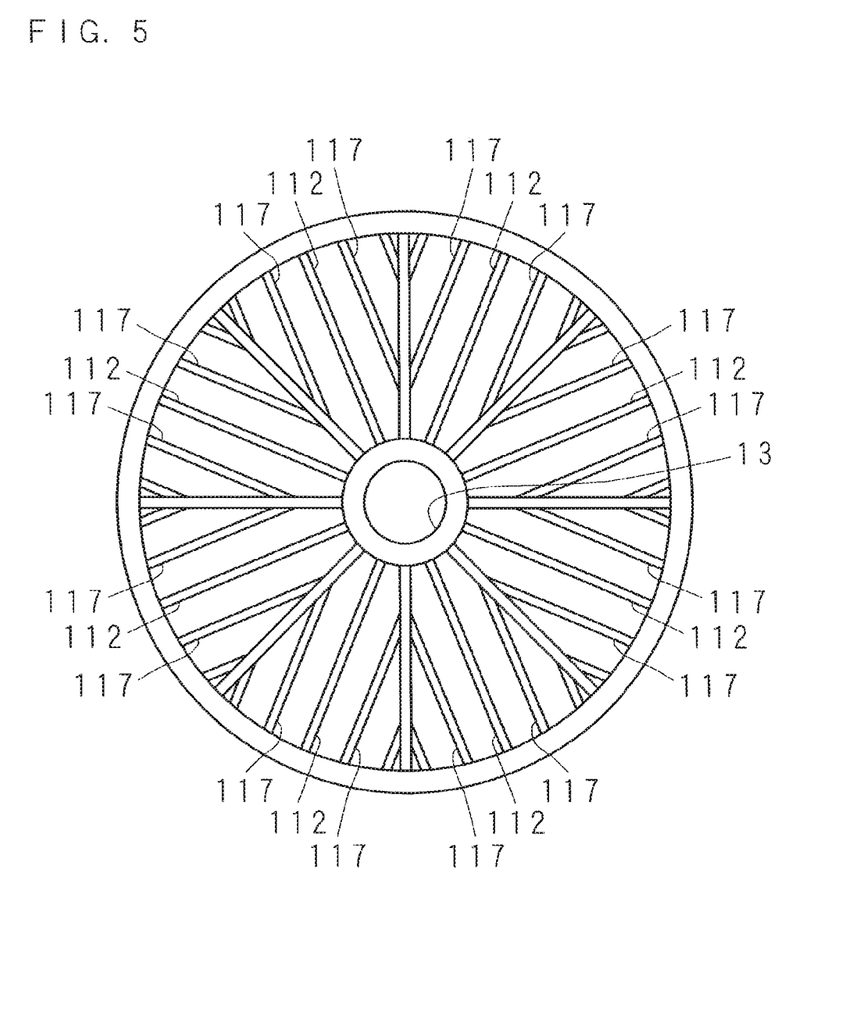
FIG. 5 is a schematic plan view of an X-ray transmissive window according to Embodiment 2.

FIG. 5 is a schematic plan view of an X-ray transmissive window 11 according to Embodiment 2. A plurality of ribs in the X-ray transmissive window 11 include a plurality of linear ribs 112 formed radially with a center at a through-hole 13, and linear parallel ribs (fourth ribs) 117 formed parallel to the linear ribs 112. The X-ray spectroscopic analyzer has a structure similar to Embodiment 1 except the X-ray transmissive window 11.

The probability that the linear ribs 112 block characteristic X-rays entering the X-ray transmissive window 11 does not change according to the incidence angles of the characteristic X-rays as in Embodiment 1. Moreover, the parallel ribs 117 provide an effect equivalent to the linear ribs 112. That is, although the probability that the parallel ribs 117 block the characteristic X-rays becomes slightly higher as the incidence angles of the characteristic X-rays become shallower, the parallel ribs 117 are parallel to the linear ribs 112, and thus the area to block the characteristic X-rays is small and the probability that characteristic X-rays entering at shallow angles are blocked is suppressed. Therefore, the probability that characteristic X-rays entering at shallow angles with respect to the X-ray transmissive window 11 are blocked is sufficiently lower than a conventional X-ray transmissive window. Accordingly, more characteristic X-rays are transmitted through the X-ray transmissive window 11 and detected by the X-ray detection elements 12 also in this embodiment than in a case where a conventional X-ray transmissive window is used, and thus the detection efficiency of characteristic X-rays by the X-ray detector 1 is enhanced.

Embodiment 3

Figure 6:
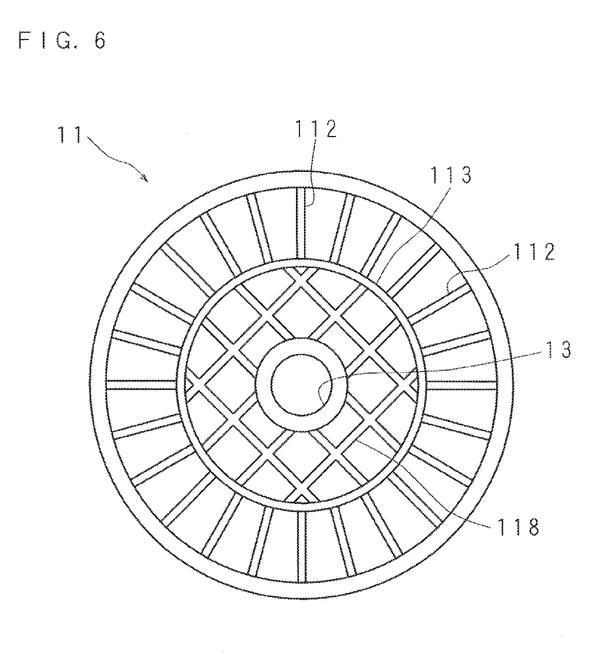
FIG. 6 is a schematic plan view of an X-ray transmissive window according to Embodiment 3.

FIG. 6 is a schematic plan view of an X-ray transmissive window 11 according to Embodiment 3. A plurality of ribs in the X-ray transmissive window 11 include a plurality of linear ribs 112 formed radially with a center at a through-hole 13, an annular rib 113 formed to surround the through-hole 13, and a mesh rib 118 formed in a mesh form. The annular rib 113 is located so that the through-hole 13 is placed at the center thereof. Moreover, an X-ray transmissive film 111 includes a region (first region) closer to the through-hole 13 than the annular rib 113, and a region (second region) farer from the through-hole 13 than the annular rib 113. The linear ribs 112 are formed in the region farer from the through-hole 13 than the annular rib 113, and the mesh rib 118 is formed in the region closer to the through-hole 13 than the annular rib 113. The X-ray spectroscopic analyzer has a structure similar to Embodiment 1 except the X-ray transmissive window 11.

Since a region in the X-ray transmissive window 11 where the mesh rib 118 is formed is close to the through-hole 13, characteristic X-rays radially emitted from one point on a line extending through the through-hole 13 enter at angles equivalent to perpendicular with respect to a region where the mesh rib 118 is formed. Since characteristic X-rays enter the X-ray transmissive window 11 at deep angles, the probability that the mesh rib 118 blocks the characteristic X-rays is low. Moreover, the mesh rib 118 firmly supports the X-ray transmissive film 111. Although characteristic X-rays enter a region in the X-ray transmissive window 11 where the linear ribs 112 are formed at shallow angles, characteristic X-rays are transmitted through said region with a probability equivalent to characteristic X-rays entering perpendicularly as in Embodiment 1. Accordingly, more characteristic X-rays are transmitted through the X-ray transmissive window 11 and detected by the X-ray detection elements 12 also in this embodiment than in a case where a conventional X-ray transmissive window is used, and thus the detection efficiency of characteristic X-rays by the X-ray detector 1 is enhanced.

Figure 7:
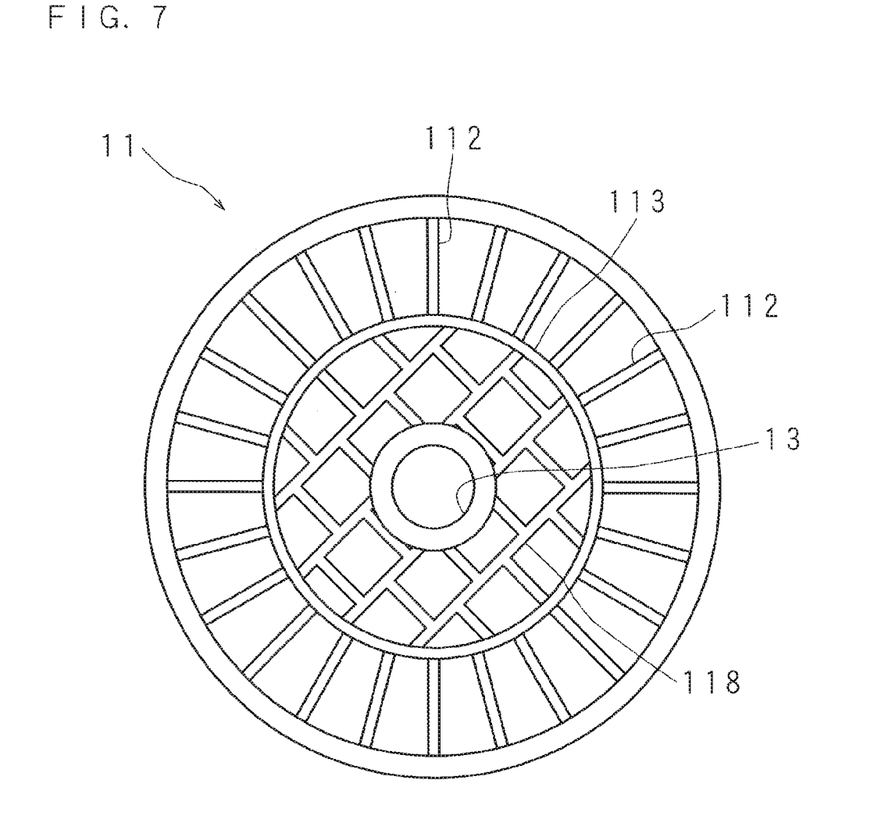
FIG. 7 is a schematic plan view illustrating another example of an X-ray transmissive window according to Embodiment 3.
Figure 8:
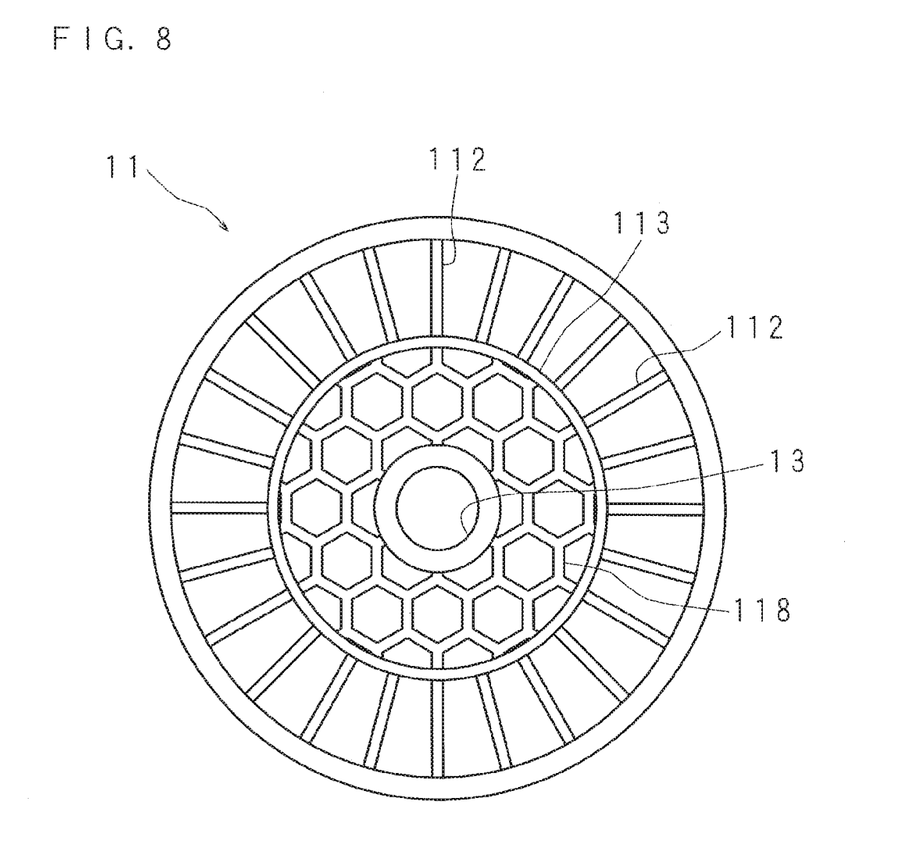
FIG. 8 is a schematic plan view illustrating another example of an X-ray transmissive window according to Embodiment 3.

It is to be noted that the shape of the mesh rib 118 illustrated in FIG. 6 is only an example, and the mesh rib 118 may have another shape. FIGS. 7 and 8 are schematic plan views illustrating other examples of an X-ray transmissive window 11 according to Embodiment 3. FIG. 7 illustrates an example wherein the relative positions of a plurality of meshes formed in the mesh rib 118 deviate from the example in FIG. 6. FIG. 8 illustrates an example wherein the shape of the mesh rib 118 is a honeycomb form. The shape of the mesh rib 118 may be another shape, such as a shape wherein meshes having different shapes are mixed. Moreover, the X-ray transmissive window 11 may be provided with no annular rib 113, or may be provided with a plurality of annular ribs 113 having different diameters.

Embodiment 4

Figure 9:
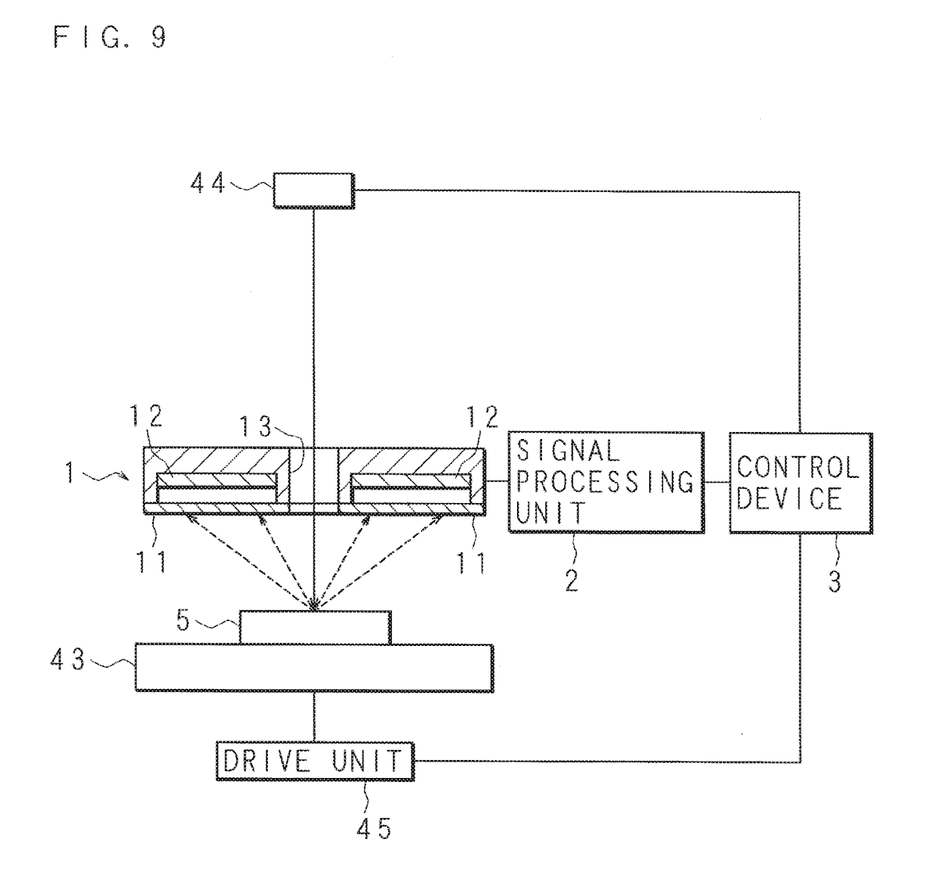
FIG. 9 is a block diagram illustrating the structure of an X-ray spectroscopic analyzer according to Embodiment 4.

FIG. 9 is a block diagram illustrating the structure of an X-ray spectroscopic analyzer according to Embodiment 4. The X-ray spectroscopic analyzer is not provided with an electron gun 41 and an electron lens system 42, and is provided with an X-ray source (irradiation unit) 44 and a drive unit 45 for moving a sample stage 43 in a horizontal direction. The X-ray source 44 is constituted of an X-ray tube. The X-ray source 44 irradiates a sample 5 on the sample stage 43 with an X-ray beam. An X-ray detector 1 is located between the X-ray source 44 and the sample stage 43. The X-ray detector 1 has a structure similar to Embodiment 1, 2 or 3. The X-ray detector 1 detects fluorescent X-rays generated from the sample 5 by irradiation with an X-ray beam. A signal processing unit 2 obtains a spectrum of fluorescent X-rays on the basis of signals outputted from the X-ray detector 1. The control device 3 executes processing to control the operation of the drive unit 45 so as to move the sample stage 43 in a horizontal direction, and irradiate the sample 5 on the moved sample stage 43 with an X-ray beam so as to scan the sample 5 with an X-ray beam. The signal processing unit 2 sequentially generates a fluorescent X-ray spectrum in accordance with scanning, and the control device 3 generates distribution of a fluorescent X-ray spectrum.

As in Embodiments 1 to 3, more fluorescent X-rays are transmitted through the X-ray transmissive window 11 and detected by the X-ray detection elements 12 also in this embodiment than in a case where a conventional X-ray transmissive window is used, and thus the detection efficiency of fluorescent X-rays by the X-ray detector 1 is enhanced. Moreover, the X-ray detector 1 in the X-ray spectroscopic analyzer similarly can be located closer to the sample 5 than a conventional structure, and thus the detection efficiency of fluorescent X-rays is enhanced in comparison with a conventional structure. Accordingly, the X-ray spectroscopic analyzer can more efficiently detect fluorescent X-rays generated from the sample 5 than a conventional structure.

Embodiment 5

Figure 10:
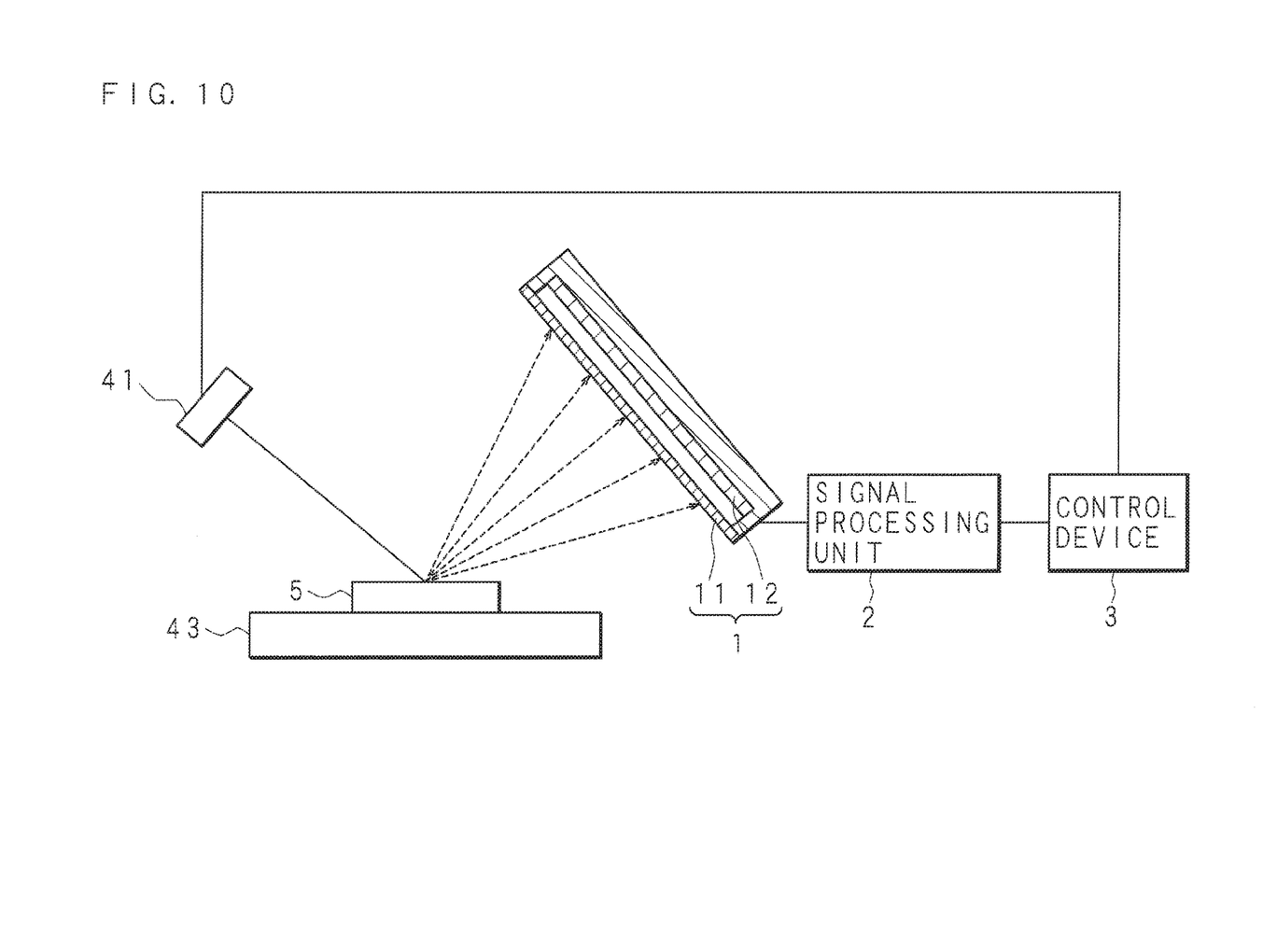
FIG. 10 is a block diagram illustrating the structure of an X-ray spectroscopic analyzer according to Embodiment 5.

FIG. 10 is a block diagram illustrating the structure of an X-ray spectroscopic analyzer according to Embodiment 5. The X-ray spectroscopic analyzer is not provided with an electron lens system 42. Moreover, an X-ray detector 1 is located at a position deviated from a position between an electron gun 41 and a sample stage 43. The electron gun 41 irradiates a sample 5 on the sample stage 43 with an electron ray. The X-ray detector 1 detects characteristic X-rays generated from the sample 5 by irradiation with an electron ray. A signal processing unit 2 obtains a spectrum of characteristic X-rays on the basis of signals outputted from the X-ray detector 1. A control device 3 controls the electron gun 41 and stores data of the spectrum of characteristic X-rays. It is to be noted that the control device 3 may make qualitative analysis or quantitative analysis of elements included in the sample 5 from the spectrum of characteristic X-rays.

Figure 11:
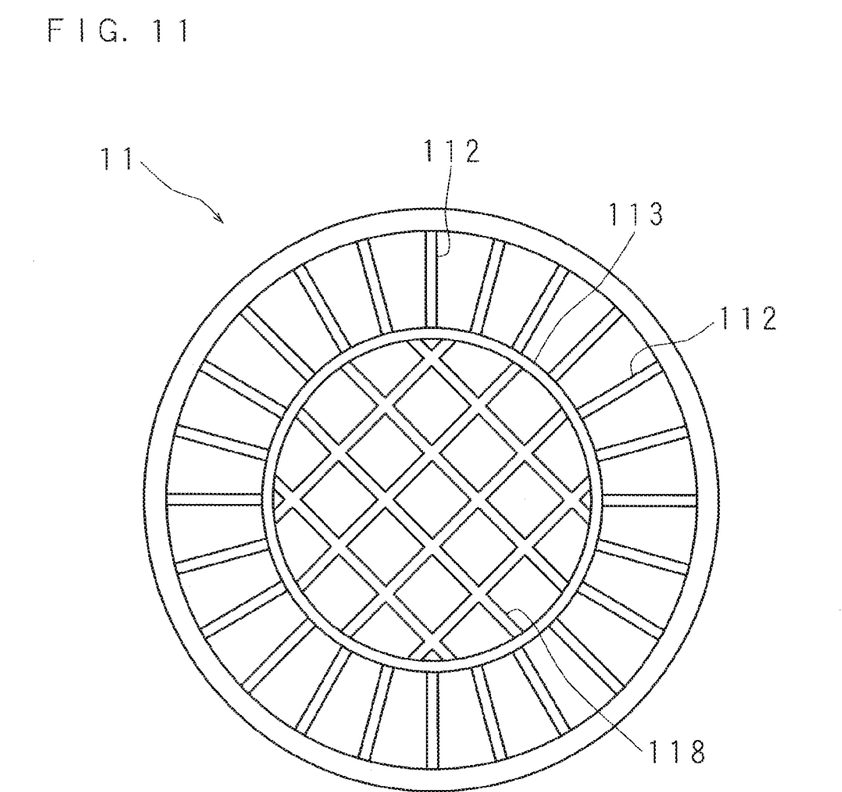
FIG. 11 is a schematic plan view of an X-ray transmissive window according to Embodiment 5.

The X-ray detector 1 is not provided with a through-hole 13. FIG. 11 is a schematic plan view of an X-ray transmissive window 11 according to Embodiment 5. A plurality of ribs in the X-ray transmissive window 11 include a plurality of linear ribs 112, which are formed radially with a center at a predetermined one point, an annular rib 113, and a mesh rib 118. An X-ray transmissive film 111 includes a region (first region) on the inner side of the annular rib 113 and a region (second region) on the outer side. One point at the center of the radial linear ribs 112 is included in the region on the inner side of the annular rib 113. The linear ribs 112 are formed in the region on the outer side of the annular rib 113, and the mesh rib 118 is formed in the region on the inner side of the annular rib 113. It is to be noted that the shape of the mesh rib 118 may be another shape such as a honeycomb form as in Embodiment 3. Moreover, the X-ray transmissive window 11 may be provided with no annular rib 113, or may be provided with a plurality of annular ribs 113 having different diameters.

Characteristic X-rays generated at the sample 5 are emitted from one point irradiated with an electron beam toward all directions also in this embodiment. The X-ray detector 1 is located so that a point on the sample 5 to be irradiated with an electron ray is placed on a line perpendicular to a region in the X-ray transmissive window 11 where the mesh rib 118 is formed. Characteristic X-rays are generated radially with a center at a line perpendicular to a region where the mesh rib 118 is formed, and enter the X-ray detector 1. The characteristic X-rays enter at angles equivalent to perpendicular with respect to a region in the X-ray transmissive window 11 where the mesh rib 118 is formed. Since the characteristic X-rays enter the X-ray transmissive window 11 at deep angles, the probability that the mesh rib 118 blocks the characteristic X-rays is low. Although characteristic X-rays enter a region in the X-ray transmissive window 11 where the linear ribs 112 are formed at shallow angles, the characteristic X-rays are transmitted through said region with a probability equivalent to characteristic X-rays entering perpendicularly as in Embodiment 1. Accordingly, more characteristic X-rays are transmitted through the X-ray transmissive window 11 and detected by the X-ray detection elements 12 also in this embodiment than in a case where a conventional X-ray transmissive window is used, and thus the detection efficiency of characteristic X-rays by the X-ray detector 1 is enhanced. Moreover, the X-ray detector 1 in the X-ray spectroscopic analyzer similarly can be located closer to the sample 5 than a conventional structure, and thus the detection efficiency of characteristic X-rays is enhanced in comparison with a conventional structure. Accordingly, the X-ray spectroscopic analyzer can detect characteristic X-rays generated from the sample 5 more efficiently than a conventional structure.

It is to be noted that the X-ray transmissive window 11 may be provided with no mesh rib 118 as illustrated in Embodiment 1 or 2. Moreover, the X-ray spectroscopic analyzer may have a form wherein an electron gun 41 is not provided, an X-ray source 44 is provided, a sample 5 is irradiated with an X-ray beam, and fluorescent X-rays generated from the sample 5 are detected by the X-ray detector 1.

It is to be noted that, although Embodiments 1 to 5 described above illustrate forms wherein a sample 5 is irradiated with an electron ray or an X-ray, an X-ray spectroscopic analyzer may have a form wherein a sample 5 is irradiated with other radiation. For example, an X-ray spectroscopic analyzer may be designed to irradiate a sample 5 with a beam of charged particles. Moreover, although the X-ray detection elements 12 in Embodiments 1 to 5 are SDDs, X-ray detection elements 12 may be detection elements other than SDDs. Moreover, an X-ray detector 1 may be a detector other than a semiconductor detector. Moreover, although Embodiments 1 to 5 illustrate forms of energy dispersion type for detecting X-rays separately for each energy, an X-ray spectroscopic analyzer may have a form of wavelength dispersion type for detecting X-rays separately for each wavelength. Moreover, a radiation detector and a radiation detection apparatus according to the present invention may be designed to detect radiation other than X-rays. Moreover, a radiation detection apparatus according to the present invention may have a form wherein a function of irradiating to a sample with a beam is not provided.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A radiolucent window, comprising:
a film which transmits radiation; and
a plurality of ribs formed on one face of the film, each rib of the plurality of ribs is individually connected to and formed integrally with the film,
wherein the plurality of ribs include
a plurality of linear ribs formed radially with a center at a predetermined one point,
a peripheral rib which has an annular shape and is formed at a peripheral part of the film, and
an annular rib which is formed to surround the predetermined one point and is formed at between the predetermined one point and the peripheral rib, and
wherein ribs located at between the annular rib and the peripheral rib are only the plurality of linear ribs.

2. The radiolucent window according to claim 1,
wherein the annular rib has a smaller height from the one face than the plurality of linear ribs.

3. The radiolucent window according to claim 1,
wherein the number of the plurality of ribs formed at between the annular rib and the peripheral rib is larger than the number of the plurality of ribs formed at between the predetermined one point and the annular rib.

4. The radiolucent window according to claim 1,
wherein the plurality of ribs include
a mesh rib formed at between the predetermined one point and the annular rib.

5. A radiation detector comprising:
a radiolucent window according to claim 1; and
an element for detecting radiation transmitted through the radiolucent window.

6. A radiation detection apparatus comprising:
an irradiation unit for irradiating a sample with a beam; and
a radiation detector for detecting radiation generated from a part on the sample irradiated with the beam,
wherein the radiation detector includes
a radiolucent window according to claim 1, and
an element for detecting radiation transmitted through the radiolucent window.

7. The radiolucent window according to claim 1, wherein the plurality of ribs are made of silicon or diamond.

8. The radiolucent window according to claim 1, wherein the film is an organic film or a CVD film.

9. The radiolucent window according to claim 1, further comprising an etching stop layer interposed between the film and the plurality of ribs.

10. The radiolucent window according to claim 1, wherein the each rib of the plurality of ribs is individually connected to the film by a surface of the each rib facing the film.

* * * * *